(12) United States Patent
Rincón Orozco

(10) Patent No.: US 11,406,366 B2
(45) Date of Patent: Aug. 9, 2022

(54) DEVICE FOR COLLECTING BIOLOGICAL SAMPLES

(71) Applicant: UNIVERSIDAD INDUSTRIAL DE SANTANDER, Bucaramanga (CO)

(72) Inventor: Bladimiro Rincón Orozco, Bucaramanga (CO)

(73) Assignee: Universidad Industrial de Santander, Bucaramanga (CO)

( * ) Notice: Subject to any disclaimer, the term of this patent is extended or adjusted under 35 U.S.C. 154(b) by 183 days.

(21) Appl. No.: 16/335,872

(22) PCT Filed: Sep. 22, 2017

(86) PCT No.: PCT/IB2017/055764
§ 371 (c)(1),
(2) Date: Apr. 29, 2019

(87) PCT Pub. No.: WO2018/055564
PCT Pub. Date: Mar. 29, 2018

(65) Prior Publication Data
US 2019/0307437 A1  Oct. 10, 2019

(30) Foreign Application Priority Data
Sep. 23, 2016 (CO) .................. NC2016/0002338

(51) Int. Cl.
*A61B 10/02* (2006.01)
*A61B 90/00* (2016.01)
(52) U.S. Cl.
CPC .. *A61B 10/0291* (2013.01); *A61B 2010/0208* (2013.01); *A61B 2010/0216* (2013.01); *A61B 2090/0817* (2016.02)
(58) Field of Classification Search
None
See application file for complete search history.

(56) References Cited

U.S. PATENT DOCUMENTS 4,227,537 A * 10/1980 Suciu ................. A61B 10/0291
600/569
5,445,164 A   8/1995 Worthen et al.
(Continued)

FOREIGN PATENT DOCUMENTS

CN       104622518 A    5/2015
WO         9622053 A1    7/1996
(Continued)

OTHER PUBLICATIONS

Rovers Medical Devices BV, Evalyn Brush instructions for the home test, Sep. 2011.

*Primary Examiner* — Benjamin S Melhus
(74) *Attorney, Agent, or Firm* — The Morales Law Firm; Joseph L. Morales

(57) ABSTRACT

A device for the collection of biological samples comprising a cylindrical body with a proximal end and a distal end. In addition, the cylindrical body includes a tab located within the cylindrical body, between the proximal end and the distal end; and a stop located on the inner surface of the cylindrical body between the proximal end and the distal end. In addition, the device includes a rod located within the cylindrical body, wherein the rod has a proximal tip and a distal tip sticking out from the distal end of the cylindrical body; and a tab located between the proximal tip and the distal tip. Also, the device includes a brush with a distal connection connected to the proximal tip of the rod, wherein the distal connection is located apart from the stop in the proximal direction. On the other hand, when the rod moves longitudinally along the cylindrical body in the proximal direction, the rod connects the flange to the tab. Furthermore, when the rod moves longitudinally along the cylindrical body in the distal direction, it causes the distal connection of the brush (Continued)

to strike against the cylindrical body stop, causing the brush to detach from the rod.

10 Claims, 5 Drawing Sheets

(56) References Cited

U.S. PATENT DOCUMENTS

| | | | | |
|---|---|---|---|---|
| 5,456,265 A * | 10/1995 | Yim | ............ | A61B 10/0291 |
| | | | | 600/569 |
| 5,795,309 A | 8/1998 | Leet et al. | | |
| 6,346,086 B1 | 2/2002 | Maksem et al. | | |
| 6,346,087 B1 * | 2/2002 | Peltier | ............ | A61B 10/0096 |
| | | | | 600/569 |
| 6,352,513 B1 * | 3/2002 | Anderson | ............ | A61B 10/0045 |
| | | | | 600/569 |
| 6,387,058 B1 * | 5/2002 | Wallach | ............ | A61B 10/0291 |
| | | | | 600/569 |
| 7,517,323 B2 * | 4/2009 | Ng | ............ | A61B 10/0045 |
| | | | | 600/569 |
| 7,749,173 B2 * | 7/2010 | Larkin | ............ | A61B 10/02 |
| | | | | 600/569 |
| 8,323,211 B2 * | 12/2012 | Larkin | ............ | A61B 10/0045 |
| | | | | 600/569 |
| 10,448,934 B2 | 10/2019 | Zwart | | |
| 2003/0088190 A1 * | 5/2003 | Inoue | ............ | A61B 10/0045 |
| | | | | 600/562 |
| 2005/0288606 A1 * | 12/2005 | Alter | ............ | A61D 1/00 |
| | | | | 600/572 |
| 2007/0073186 A1 * | 3/2007 | Decker | ............ | A61B 10/0045 |
| | | | | 600/569 |
| 2008/0188769 A1 | 8/2008 | Lu | | |
| 2011/0021950 A1 * | 1/2011 | Daniels | ............ | A61B 10/02 |
| | | | | 600/569 |
| 2013/0066233 A1 | 3/2013 | Klein | | |
| 2014/0024069 A1 * | 1/2014 | Figueredo | ............ | A61B 10/0291 |
| | | | | 435/29 |
| 2014/0180165 A9 * | 6/2014 | Zwart | ............ | A61B 10/02 |
| | | | | 600/569 |
| 2016/0262734 A1 | 9/2016 | Chin-Ly | | |

FOREIGN PATENT DOCUMENTS

| | | |
|---|---|---|
| WO | 9732517 A1 | 9/1997 |
| WO | 2011021931 A1 | 2/2011 |

* cited by examiner

DEVICE FOR COLLECTING BIOLOGICAL SAMPLES

FIELD OF THE INVENTION

The present invention relates to devices for collection of biological specimen samples. Particularly, it is related to devices for the collection of gynecological samples of the cervix, which can be operated directly by the person from whom the sample must be taken.

DESCRIPTION OF PRIOR ART

US 2013/0211288 A1 discloses a device for sample collection in cavities, particularly for cervix sample collection inside the vaginal cavity. The device comprises a tube with two open ends, a sample collecting element and a plunger inserted in the tube. The distal end of the plunger sticks out from the distal end of the tube. In a removable manner, the distal end of the sample collector element is connected to the proximal end of the plunger. In addition, the prior art document discloses that the sample collecting element moves in the proximal direction of the tube.

Also, said prior art document discloses an extension limiter defining the maximum distance that the sample collector element sticks out from the tube. Additionally, a clicking mechanism with a click-type protuberance and a radial click-type tab are disclosed. The click-type protuberance is located inside the tube, or on the rod, on the other hand, the click-type radial tab is located on the rod or inside the tube, so when the rod rotates with respect to the tube a "click" sound occurs. In addition, the document discloses an insertion stop located on the outer surface of the tube, extending radially with respect to the tube. The insertion stop limits the advance of the tube in the proximal direction of the cavity.

On the other hand, the prior art discloses a sterile package in which the device is deposited before and after taking a sample, but, the package cannot be water-sealed after having been opened, for which, it is necessary to use additional bags to transport the sample and include a device which absorbs liquids that may get out of the device. However, the prior art document does not indicate how the brush should be removed from the plunger, which suggests that external elements, such as tweezers or pliers, must be used, which may contaminate the sample.

Additionally, the prior art points out that after taking the sample, the device is placed in a bag, which implies that cervical tissue and mucus may be spread in the bag and reduce the content to be analyzed in post-sample collection processes. On the other hand, the device lid does not allow a water-tight closure, which implies the possibility of the sample being spilled around the device, exposing the people who manipulate the sample to biological contamination. Also, it is identified that between the plunger and the sample-collecting element, there are spaces allowing filtrations of biological fluids, which also jeopardizes people manipulating the device, for example, laboratory technicians and doctors.

Therefore, no device for biological sample collection was found in prior art, particularly for the collection of gynecological samples, able to avoid sample contamination and/or spreading of the sample in transport containers.

Brief Description of the Invention

A device for the collection of biological samples, comprising a cylindrical body with a proximal end and a distal end. In addition, the cylindrical body includes a tab located within the cylindrical body, between the proximal end and the distal end; and a stop located on the inner surface of the cylindrical body between the proximal end and the distal end. In addition, the device includes a rod located within the cylindrical body, wherein the rod has a proximal tip and a distal tip sticking out from the distal end of the cylindrical body; and a tab located between the proximal tip and the distal tip. Also, the device includes a brush with a distal connection connected to the proximal tip of the rod, wherein the distal connection is located apart from the stop in the proximal direction. On the other hand, when the rod moves longitudinally along the cylindrical body in the proximal direction, the rod connects the flange to the tab. On the other hand, when the rod moves longitudinally along the cylindrical body in the distal direction, it causes the distal connection of the brush to strike against the cylindrical body stop, causing the brush to detach from the rod.

DETAILED DESCRIPTION

The present invention corresponds to a device for the collection of biological samples, hereinafter "device".

Figure 1:
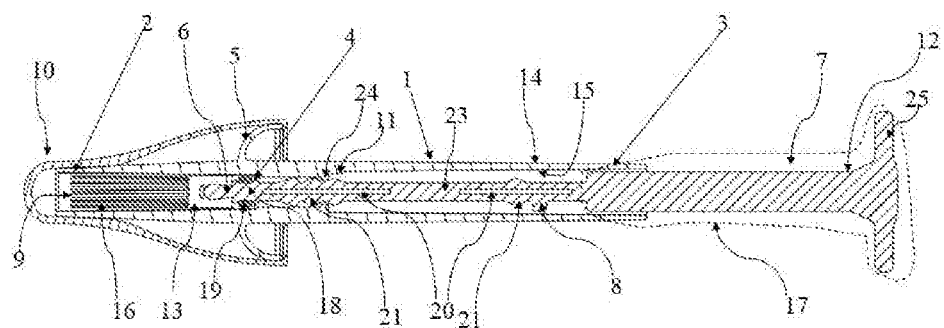
FIG. 1 corresponds to a longitudinal sectional view of one embodiment of the device for collection of biological samples.

With reference to FIG. 1, in one embodiment of the invention, the device comprises:
- a cylindrical body (1) with:
  - a proximal end (2);
  - a distal end (3);
  - a tab (11) located inside the cylindrical body (1), between the proximal end (2) and the distal end (3); and
  - a stop (4) located on the internal surface (15) of the cylindrical body (1) between the proximal end (2) and the distal end (3);
- a rod (7) located inside the cylindrical body (1), the rod (7) has:
  - a proximal tip (6);
  - a distal tip (12) protruding from the distal end (3) of the cylindrical body (1);
  - a flange (8), located between the proximal tip (6) and the distal tip (12); Y
- brush (9) with a distal connection (13) connected to the proximal tip (6) of the rod (7), the distal connection (13) is located adjacent to the stop (4)

In one embodiment of the invention, the cylindrical body (1) is inserted into a conduit with a distal inlet and a sampling area located at a proximal end of the conduit.

In one embodiment of the invention, the conduit is a vaginal canal, the distal entrance is the vulva of the vagina, and the area for sampling is the cervix or uterine neck.

In one embodiment of the invention, the cylindrical body (1) has on its external surface (14) a proximal advancing stop (5) located between the proximal end (2) and the distal end (3). The proximal advancing stop (5) strikes the distal entrance of the conduit and positions the proximal end (2) within the conduit at a predetermined position. In addition, the proximal advancing stop (5) prevents the insertion of the cylindrical body (1) to be made in excess, reaching an ideal distance for taking samples of the conduit.

In one embodiment of the invention, the distance between the proximal end (2) and the distal end (3) of the cylindrical body (1) is between 5 and 20 cm. The distance between the proximal end (2) and the proximal advancing stop (5) is between 20 and 60 mm. This distance corresponds to the average size of the female vaginal conduit, therefore, the device allows an ergonomically fit in the female vaginal conduit, in order to obtain a sample of the cervix with the brush (9). On the other hand, the distance between the proximal end (2) and the distal end (3) can be between 5 cm and 7 cm, between 7 cm and 9 cm, between 9 cm and 12 cm, between 12 cm and 15 cm, between 15 cm and 17 cm, or between 17 cm and 20 cm.

In one embodiment of the invention, the conduit is a vaginal canal, the proximal advancing stop (5) has an external diameter, and a curvature in the distal direction that allows the proximal advancing stop (5) to be accommodated in the *Labia minora* of the vagina, in order to avoid hurting other parts of the vulva.

In one embodiment of the invention, the proximal advancing stop (5) is located at a distance between 20 mm and 50 mm from the proximal end (2) of the cylindrical body (1). The proximal advancing stop (5) is located at a distance between 20 mm and 60 mm from the proximal end (2) of the cylindrical body (1) ensuring that when the device is inserted into a vagina and when moving the brush in the proximal direction (9) by means of the rod (7) there is contact with the cervix. The proximal advancing stop (5) can be located between 20 mm and 25 mm, between 25 mm and 27 between 27 mm and 32 m, between 32 mm and 38 mm, between 38 mm and 42 mm, between 42 mm and 46 mm, or between 46 mm and 50 mm from the end proximal (2) of the cylindrical body (1).

In one embodiment of the invention, the cylindrical body (1), the tab (11), the stop (4) and the proximal advancing stop (5) form a monolithic body. The monolithic body is designed anatomically for the total comfort of the user whose sample is taken and is made of a biocompatible plastic material.

For purposes of interpreting the present invention, biocompatible material will be understood as a material complying with ISO-10993: "Biological Evaluation of Medical Devices". Some materials are: Polyaryletherketone (PAEK), polyetheretherketone (PEEK), high density polyethylene (HDPE), ultra high molecular weight polyethylene (UHMWPE), polymethylmethacrylate (PMMA), Commercially Pure Titanium (ASTM F67), Titanium Alloys ASTM B265 (standard specification of titanium and titanium in the form of strip, sheet and plate) and Stainless Steel AISI 316L, Acryl Butadiene Styrene (ABS) medical grade, polycarbonate, polyamide, polyester, polyvinyl chloride (PVC), polypropylene and polystyrene. Preferably the monolithic body is made of polypropylene and polystyrene.

Figure 2:
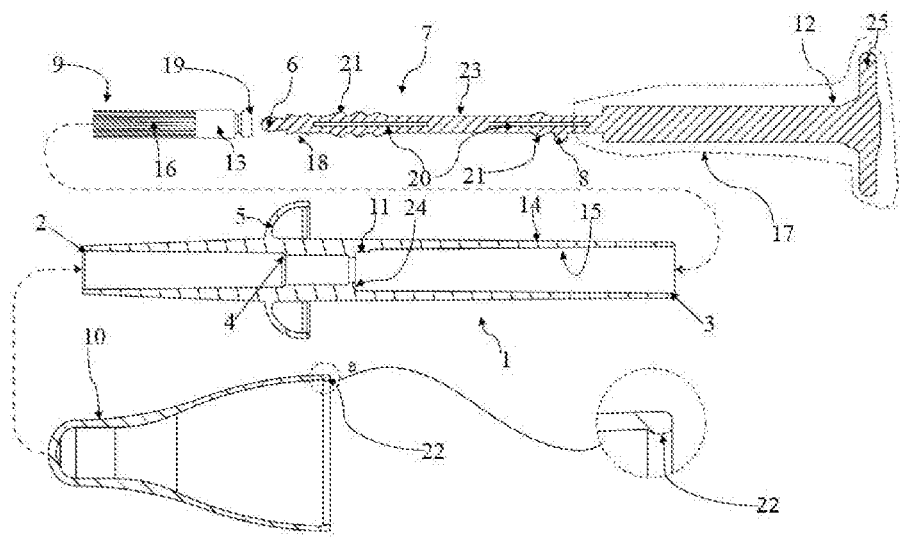
FIG. 2 corresponds to an exploded view of a device embodiment for collecting biological samples.
Figure 3:
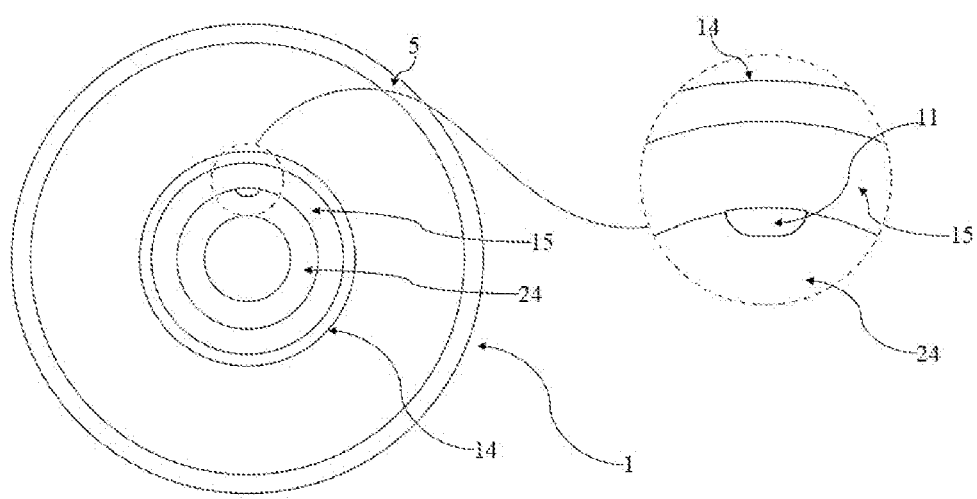
FIG. 3 corresponds to a detailed view of a tab of a embodiment of the device for collection of biological samples.

With reference to FIG. 1 and FIG. 3, in one embodiment of the invention, the tab (11) is a protuberance located on the inner surface (24) of the cylindrical body (1). The protuberance can be cylindrical with circular, square, polygonal, triangular or combinations of the above. Also, the protuberance may be a hemisphere sticking out from the inner surface (15). Preferably, the protuberance is cylindrical with a square cross section, furthermore, the protuberance has its rounded edges. The rounding of the edges makes it possible to reduce the stresses generated by the flange (8) which hits the tab (11) when the rod (7) rotates with respect to the cylindrical body (1), With reference to FIG. 1 and FIG. 2, in one embodiment of the invention, the stop (4) of the cylindrical body (1) is a section change of the inner surface (15) of the cylindrical body (1) with a larger diameter in the proximal direction than in the distal direction. The section change is located between the proximal end (2) and the distal end (3) of the cylindrical body (1).

In a non-illustrated embodiment, the stop (4) is a ring-shaped protuberance, disposed between the proximal end (2) and the distal end (3) of the cylindrical body (1).

In one embodiment of the invention, the stop (4) is located at a distance from the proximal end (2) which can be, between 10 mm and 50 mm, between 10 mm and 15 mm, between 15 mm and 20 mm, between 20 mm and 25 mm, between 25 mm and 30 mm, between 30 mm and 35 mm, between 35 mm and 40 mm, between 40 mm and 45 mm or between 45 mm and 50 mm. Preferably, the stop (4) is located at a distance from the proximal end (2) around 45 mm, allowing the displacement of the rod (7) at an ideal distance for taking the sample.

Ideal distance will be understood as a distance measured from the uterine neck towards the distal direction of the vaginal canal to the proximal end (2) of the cylindrical body (1) sufficient for the rod (7) to be able to move in the proximal direction and connect.

In one embodiment of the invention, the cylindrical body (1) includes a ring (24) located between the tab (11) and the stop (4), the ring (24) is at a distance from the tab (11) that may be between 1 mm and 10 mm, between 1 mm and 3 mm, between 3 mm and 5 mm, between 5 mm and 8 mm or between 8 mm and 10 mm.

With reference to FIG. 2, in one embodiment of the invention, the rod (7) includes a handle (17) located on the distal tip (12) of the rod (7), the handle (17) has at its distal end a crank (25) which facilitates the grip of the rod, and allows a user to rotate the rod (7) with respect to the cylindrical body (1) in an ergonomic manner, to rotate the rod (7) in a clockwise direction, and also in the opposite direction to clock hands. The crank (25) has a star shape with rounded tips and vertices, designed for comfort and good grip of the user, preventing the user from cutting or injuring when grabbing the crank (25). The star-shaped crank (25) may have three, four, five, six, seven, eight, nine, or ten points. Also, the star-shaped crank (25) may have more than ten rounded tips. The star shape of the crank (25) is circumscribed in a circumference of a diameter that may be between 25 mm and 40 mm, between 25 mm and 30 mm, between 30 mm and 35 mm, or between 35 mm and 40 mm.

Figure 4:
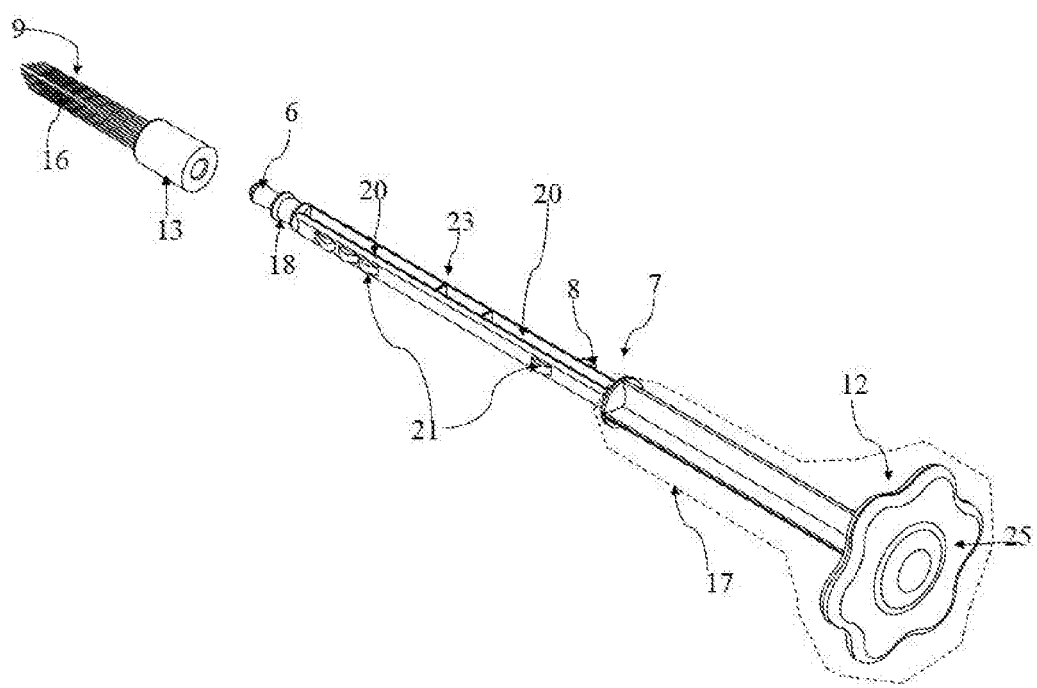
FIG. 4 corresponds to an isometric view of a rod and a brush of one embodiment of the device for collection of biological samples.

With reference to FIG. 4, in one embodiment of the invention, the crank (25) has an eight-pointed star shape, the star has rounded tips and vertices. The crank (25) is circumscribed in a circumference with a diameter between 25 and 45 mm.

Also, the rod (7) has a central section (23) that extends between the proximal end of the handle (17) and the proximal tip (6) of the rod (7). In the central section (23) there is located a first and a second longitudinal slot (20), which are located on the cross axis of the rod (7). The first longitudinal slot (20) is located next to the proximal end of the handle (17). On the other hand, in the radial direction of the rod (7) the flange (8) and two protuberances (21) extend. The protuberances (21) are located next to the flange (8) in the proximal direction. Preferably, the protuberances (21) are distributed symmetrically with respect to the first longitudinal slot (20).

On the other hand, the second longitudinal slot (20) is located near the proximal tip (6) of the rod (7). Around the second longitudinal slot (20) protuberances (21) are distributed axially symmetrically. In one embodiment of the invention, six protuberances (21) grouped in three pairs are arranged, each pair having two protuberances (21) spaced apart symmetrically with respect to the cross axis of the rod (7).

With reference to FIG. 1, in one embodiment of the invention, the protuberances (21) located around the second longitudinal slot (20) interact with the ring (24) of the cylindrical body (1) in the following manner:

When the rod (7) moves longitudinally with respect to the cylindrical body (1) in the proximal direction, the ring (24) shackles the protuberances (21) and elastically deforms the second longitudinal slot (20).

With reference to FIG. 1, in one embodiment of the invention, the rod (7) has a proximal housing (18) located between the proximal tip (6) and the central section (23). In the proximal housing (18) which is connected to a gasket (19). The gasket (19) and the internal surface (15) near the proximal end (2) of the cylindrical body (1) form a sliding fit. In addition, the gasket (19) and the inner surface (15) generate a hermetic seal between the rod (7) and the inner surface of the cylindrical body (1), which prevents fluid passing through the cylindrical body (1) from the proximal end (2) towards the distal end (3). The above, ensures that when a biological sample is collected with the brush (9), no biological fluids pass, such as mucus and/or blood, to the distal end (3) of the cylindrical body (1), decreasing the biological risk to which a person who manipulates the device is exposed after having taken the sample, for example, a laboratory technician or a doctor.

With reference to FIG. 1 and FIG. 2, in one embodiment of the invention, the device includes a removable lid (10) which is connected and disconnected to the proximal advancing stop (5). The removable lid (10) generates a hermetic seal with the proximal advancing stop (5), which allows to maintain the content of the sample inside the cylindrical body (1), and avoids filtering fluids that are part of the sample out of the removable lid (10). This also reduces the biological risk to which a person who manipulates the device is exposed after taking the sample, for example, a laboratory worker or a doctor.

With reference to FIG. 2, in one embodiment of the invention, the removable lid (10) includes a closing flange (22) located on the open edge of the removable lid (10). In this embodiment, the removable lid (10) deforms elastically when entering the distal direction and presses the proximal advancing stop (5). When the open edge of the removable lid (10) reaches the radial edge of the proximal advancing stop (5), the closing flange (22) extends beyond said radial edge and secures the connection between the removable lid (10) and the proximal advancing stop (5). In that way, the closing flange (22) prevents displacement in the proximal direction of the removable lid (10).

Figure 5:
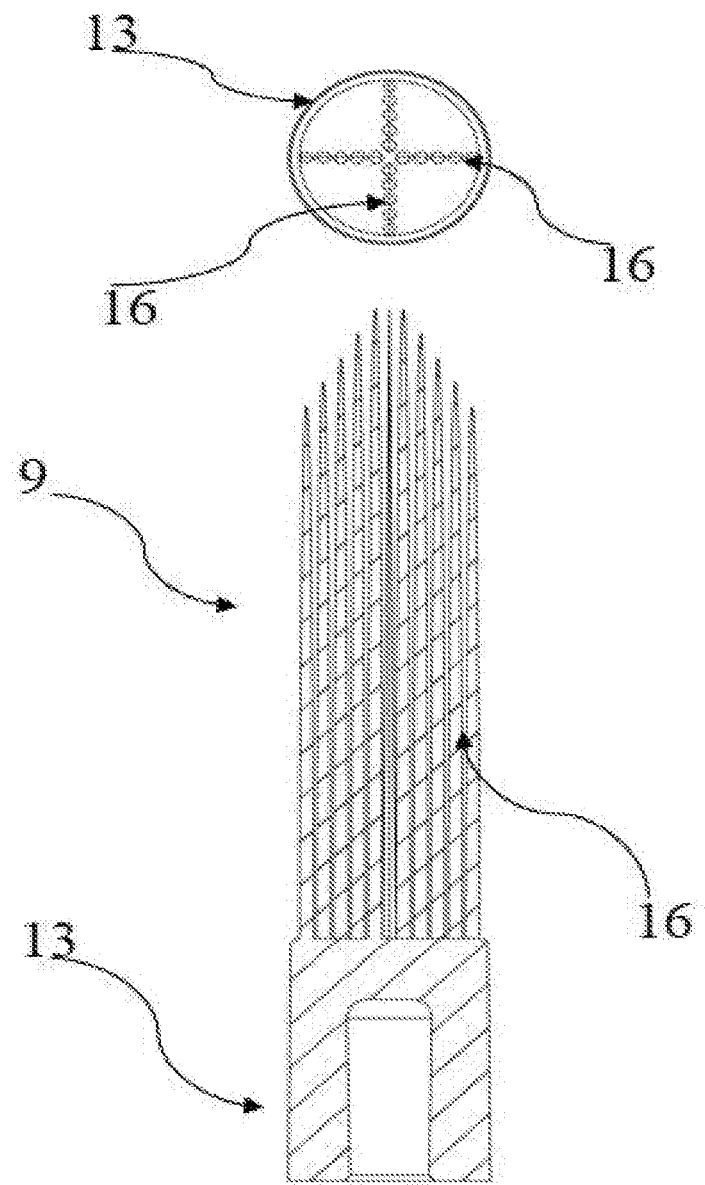
FIG. 5 corresponds to a longitudinal sectional view of a brush of one embodiment of the device for collection of biological samples.

With reference to FIG. 5, in one embodiment of the invention, the device has a brush (9) with a distal connection (13), wherein the distal connection (13) is assembled to the distal end of the rod (7). The brush (9) has a total length that can be between 20 mm and 25 mm, 25 mm and 30 mm, 30 mm and 35 mm or 30 mm and 40 mm. The brush (9) is composed of two rows of bristles (16) arranged in the shape of a cross. Preferably, each row of bristles (16) has longer bristles at the center of the row than at the ends of the row. The above, ensures a correct intake of the area of the cervix and the endocervix. The rows of bristles (16) have a length between 20 mm and 25 mm, 23 mm, 35 mm, 30 mm and 40 mm. In addition, the rows of bristles (16) have a maximum diameter that may be between 5 mm and 6 mm, 5 mm and 7 mm, 6 mm, or 8 mm. The distal connection (13) of the brush has a diameter that may be between 5 mm and 6 mm, 5 mm and 7 mm, 6 mm, or 8 mm.

In one embodiment of the invention, the length of the rows of bristles (16) may be between 20 mm and 25 mm, 25 mm and 30 mm, 30 mm and 35 mm or 30 mm and 40 mm. The outer row of bristles (16) has a total length between 20 mm and 25 mm, 25 mm, 30 mm or 30 mm and 35 mm with a diameter between 5 mm and 6 mm, 6 mm and 7 mm and 7 mm and 8 mm. On the other hand, the length of the inner row of bristles (16) has a total length between 20 mm and 25 mm, 25 mm, 30 mm or 30 mm and 35 mm with a diameter between 2 mm and 3 mm, 3 mm and 4 mm and 3.5 mm and 4.5 mm.

The distal connection (13) of the brush has a diameter that may be between 5 mm and 6 mm, 5 mm and 7 mm, 6 mm, or 8 mm. The brush (9) is composed of a biocompatible plastic material which may be, Acryl Butadiene Styrene (ABS), medical grade, polycarbonate, polyamide, polyester, polyvinyl chloride (PVC), polypropylene, thermoplastic elastomer base styrene and polystyrene. Preferably it is styrene and polystyrene.

Figure 6:
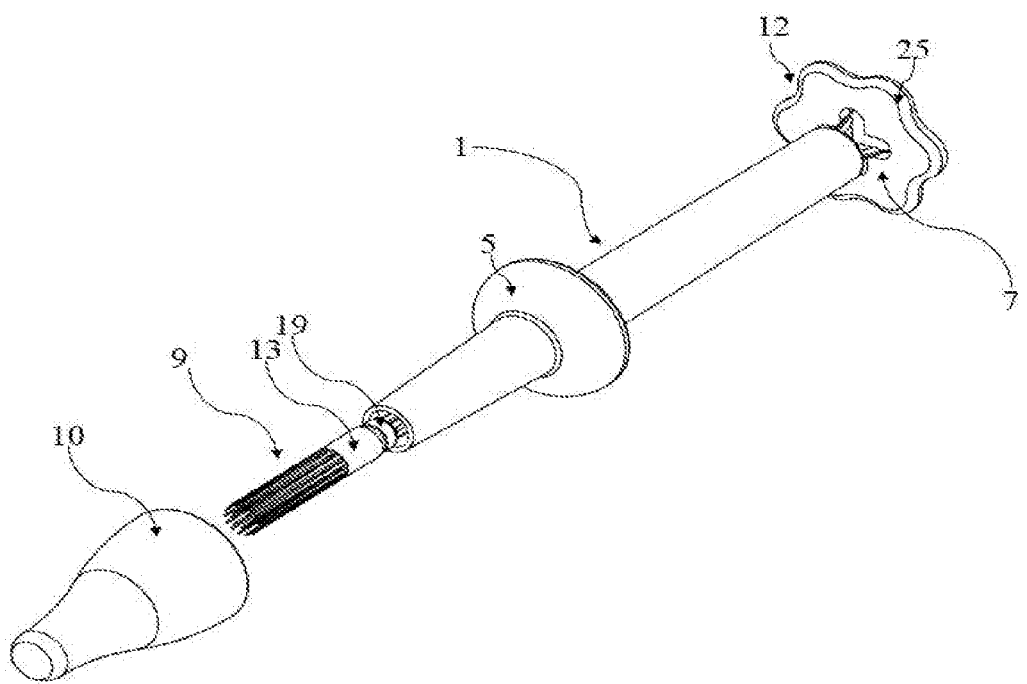
FIG. 6 corresponds to an isometric view of a embodiment of the device for collection of biological samples.

With reference to FIG. 1 and FIG. 6, in one embodiment of the invention, a method for taking biological samples with the device comprises the following steps:
A) pull out the removable lid (10) from the cylindrical body (1);
B) insert the proximal end (2) of the cylindrical body (1) into the vaginal canal until the proximal advancing stop (5) touches the *Labia minora* of the vagina;
C) grasp the crank (25) and push the rod (7) longitudinally in the proximal direction, in this step, the rod (7) moves longitudinally along the cylindrical body (1) in the proximal direction and connects the flange (8) with the tab (11), in addition, the rod (7) removes the brush (9) from the cylindrical body (1) and touches the cervix;
D) turn with the crank (25) the rod (7) with respect to the cylindrical body (1), with each rotation, the flange (8) of the rod (7) hits the tab (11) of the cylindrical body, which generates the elastic deformation of the tab (8) and produces a sound, for example, a click; the crank (25) is rotated to count a finite number of sounds (clicks), for example, between four and six clicks, preferably five clicks, in this way, the brush (9) in contact with the cervix takes the biological sample, which may contain tissue, mucus and/or blood;
E) pull the rod (7) with respect to the cylindrical body (1) in the distal direction, when the protuberances (21) located near the proximal end of the rod (7) pass the ring (24), the user feels the jumps generating the protuberances (21) when passing, when feeling the jumps, the user stops pulling the rod (7);
F) remove the proximal end (2) of the cylindrical body (1) from the vaginal canal; and G) put the removable lid (10), pushing the removable lid (10) in the distal direction until reaching the proximal advancing stop (5) with sufficient force to generate a hermetic connection; and
H) put the device inside a hermetic bag, preferably the hermetic bag is sent to a laboratory for the extraction and analysis of the sample.

Now, a procedure for extracting a biological sample collected with the device is explained, the extraction procedure includes the steps:
I. remove the device from the hermetic bag;
II. remove the removable lid (10) from the cylindrical body (1);
III. place the proximal end (2) of the cylindrical body (1) inside a container, for example, a plastic transport container or a test tube.
IV. pull the rod (7) related to the cylindrical body (1) in the distal direction causing the distal connection (13) of the brush (9) to collide against the stop (4) of the cylindrical body (1), causing the brush (9) to detach from the rod (7) and fall into the container of stage III;
V. bring the container with the brush (9) to a sample analysis process, for example, a liquid cytology test for detection of cervical cancer or molecular tests for detection of Human Papilloma Virus or other microorganisms causing diseases of sexual transmission.

EXAMPLE 1

Device for Self-Taking Cervical Gynecological Samples, with a Brush of Two Rows of Bristles Arranged in a Cross A device for the collection of biological samples was designed and built, particularly for the collection of cervical gynecological samples. The device may be used by the user who must take the sample, thus, avoiding going to a gynecologist who takes the sample. The device has a cylindrical body (1) with the following characteristics:
diameter of the proximal end (2): 13.7 mm
diameter of the distal end (3): 10.2 mm
diameter of the proximal advancing stop (5): 30 mm
length: 129.5 mm
distance between the proximal advancing stop (5) and the proximal end (2): 40 mm
thickness of the proximal advancing stop (5): 1.2 mm
internal diameter of the stop (4): 6.5 mm
external diameter of the stop (4): 7.5 mm
height of the tab (11): 1.5 mm
material: polystyrene
Manufacturing process through which it is manufactured: injection
On the other hand, the device has a rod (7) with the following characteristics:
total length: 151.5 mm
handle length (17): 68 mm
diameter of the handle (17) at the distal end: 35 mm
diameter of the handle (17) at the proximal end: 8.7 mm
length of the central region (23): 73.5 mm
measures of protuberances (21): between 0.7 mm and 0.6 mm measured from the cross axis of the rod (7)
length of each longitudinal slot (20): 25 mm
diameter of each longitudinal slot (20): 1 mm
diameter of the proximal housing (18): 4 mm
length of the proximal housing (18): 3 mm
material: polystyrene
Manufacturing process through which it is manufactured: injection
The device has a gasket (19) located at the distal end of the rod (7) with the following characteristics:
external diameter of 6.6 mm
internal diameter of 3.9 mm
gasket's width 3.0 mm
material: polystyrene
manufacturing process by which it is manufactured: injection
The device has a brush (9) that is assembled at the distal end of the rod (7) and has the following characteristics:
total length: 36 mm
maximum length of bristle row (16): 26 mm
minimum length of bristle row (16): 20 mm
outer diameter: 7.2 mm
internal diameter: 2.8 mm
external length of the assembly area 10 mm
internal length of the assembly area 7.5 mm
material: styrene-based thermoplastic elastomer
manufacturing process through which it is manufactured: injection

EXAMPLE 2

Device for Self-Taking Cervical Gynecological Samples Using a Brush with Bristles Arranged in Two Concentric Rings A device was designed and constructed as in example 1, to which a brush (9) is connected with bristles arranged in two concentric rings. The brush has the following characteristics:
total length: 36 mm
length of bristles (16): 26 mm
outer diameter: 7.2 mm
internal diameter: 2.8 mm
diameter of the first ring: 7.2 mm
diameter of the second ring: 5.5 mm
external length of the assembly area 10 mm
internal length of the assembly area 7.5 mm
material: styrene-based thermoplastic elastomer
manufacturing process by which it is manufactured: injection It should be understood that the present invention is not limited to the described and illustrated embodiments, and a person skilled in the art will understand that numerous variations and modifications may be made, which do not depart from the spirit of the invention, which is only defined by the following claims.

The invention claimed is:
1. A device for collecting biological samples comprising:
a cylindrical body with:
a proximal end;
a distal end;
a tab located inside the cylindrical body, between the proximal end and the distal end; and
a stop located on an internal surface of the cylindrical body between the proximal end and the distal end
a ring located between the tab and the stop;
a rod located inside the cylindrical body, where the rod comprises:
a proximal tip;
a distal tip protruding from the distal end of the cylindrical body;
a flange located between the proximal tip and the distal tip a central section that extends between the distal tip of the rod and the proximal tip of the rod;

at least one longitudinal slot disposed in a cross-section of the rod; and at least one protrusion around the at least one longitudinal slot; and a brush with a distal connection connected to the proximal tip of the rod, wherein the distal connection is located separately from the stop in a proximal direction;

wherein the at least one protrusion is located between the flange and the distal tip of the rod;

wherein the rod is configured to move longitudinally along the cylindrical body in the proximal direction and connects the flange with the tab;

wherein the rod is configured to stop moving longitudinally along the cylindrical body in the proximal direction preventing said rod from overextending from the cylindrical body when the flange and the tab are connected;

wherein the rod is configured to move longitudinally along the cylindrical body in a distal direction causing first that the ring presses the at least one protrusion and elastically deforms the at least one longitudinal slot and then causing the distal connection of the brush to collide against the stop of the cylindrical body, causing the brush to detach from the rod.

2. The device of claim 1, wherein the cylindrical body has an external surface and a proximal advancing stop located on said external surface and between the proximal end and the distal end of the cylindrical body.

3. The device of claim 1, further comprising a removable lid connected to the proximal end of the cylindrical body.

4. The device of claim 1, wherein the brush is selected from cervical buds, cervical brushes, and cervical spatulas.

5. The device of claim 1, wherein the rod and the brush are made of biocompatible materials.

6. The device of claim 1, wherein the brush has two rows of bristles protruding from the distal connection towards the proximal direction of the brush, where the two rows of bristles are disposed in a shape of a cross.

7. The device of claim 6, wherein each row of the two rows of bristles has a center and two ends, wherein said each row of bristles has longer bristles at the center than at the two ends.

8. The device of claim 1, wherein a handle with a star-shaped crank with rounded tips is located on the distal tip of the rod.

9. The device of claim 1, wherein a gasket is connected to the proximal tip of the rod which is configured to generate a water-tight seal between the rod and the internal surface of the cylindrical body.

10. The device of claim 1, wherein the rod includes:
a first longitudinal slot and a second longitudinal slot disposed in the central section of the rod;
at least two first protrusions around the first longitudinal slot; and
at least two second protrusions around the second longitudinal slot,
wherein, the first longitudinal slot and the second longitudinal slot are located on the cross-section of the rod.

* * * * *